United States Patent [19]

Metcalf et al.

[11] 4,139,563

[45] Feb. 13, 1979

[54] α-ACETYLENIC DERIVATIVES OF AMINES

[75] Inventors: Brian W. Metcalf, Strasbourg; Michel Jung, Illkirch Graffenstaden, both of France

[73] Assignee: Merrell Toraude et Compagnie, Strasbourg, France

[21] Appl. No.: 812,265

[22] Filed: Jul. 1, 1977

[51] Int. Cl.$^2$ .................. C07C 87/24; C07C 69/02; C07C 103/10; C01B 25/26

[52] U.S. Cl. .................. 260/583 H; 260/558 A; 260/558 S; 260/559 T; 260/559 A; 260/561 R; 260/561 A; 260/561 S; 260/561 N; 260/564 A; 160/570.5 S; 260/583 FF; 536/26; 560/24; 560/33; 560/157; 560/159; 560/165; 424/244; 424/300; 424/316; 424/320; 424/325; 424/330

[58] Field of Search ........ 260/583 EE, 583 H, 564 A, 260/570.5 S, 561 R, 561 A, 558 A, 559 A; 424/325, 300, 320; 560/24, 157, 165; 536/26

[56] References Cited

U.S. PATENT DOCUMENTS

| | | | |
|---|---|---|---|
| 3,024,190 | 3/1962 | Bennett et al. | 424/325 X |
| 3,160,664 | 12/1964 | Dawson | 424/325 X |
| 3,291,683 | 12/1966 | Lamb | 260/583 FF X |
| 3,320,277 | 5/1967 | Mehta et al. | 260/583 H X |
| 3,538,228 | 11/1970 | Nair | 424/325 |
| 3,960,927 | 6/1976 | Metcalf et al. | 260/561 A X |

FOREIGN PATENT DOCUMENTS 5230M 7/1967 France .................. 424/325

OTHER PUBLICATIONS

Mavrov et al., "Index Chemicus", vol. 30, #93265 (1968).
SIFA, "French Patents Abstracts", vol. 6, No. 47, p. 3:7 (1966).
Dumont et al., "Chem. Ab.", Ab. No. 66:115254r (1967).

Primary Examiner—Winston A. Douglas
Assistant Examiner—John Doll
Attorney, Agent, or Firm—L. Ruth Hattan; Eugene O. Retter; George W. Rauchfuss, Jr.

[57] ABSTRACT

Novel acetylenic derivatives of amines of the following general structure:

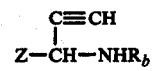

wherein Z is β-methylthioethyl, β-benzylthioethyl, S-(5'-desoxyadenosin-5'-yl)-S-methylthioethyl, γ-guanidinopropyl, or

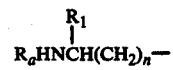

wherein n is 2 or 3 and $R_1$ is hydrogen or lower alkyl of from 1 to 4 carbon atoms with the proviso that when $R_1$ is other than hydrogen, n is 2; and each of $R_a$ and $R_b$ is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched, or

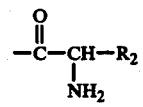

wherein $R_2$ is hydrogen, a straight or branched lower alkyl group of from 1 to 4 carbon atoms, benzyl or p-hydroxybenzyl; with the provisos that when Z is β-benzylthioethyl or S-(5'-desoxyadenosin-5'-yl)-S-methylthioethyl, $R_b$ is hydrogen, and when Z is

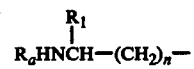

each of $R_a$ and $R_b$ can be the same or different; and pharmaceutically acceptable salts and individual optical isomers thereof.

8 Claims, No Drawings

α-ACETYLENIC DERIVATIVES OF AMINES

FIELD OF INVENTION

This invention relates to novel pharmaceutically useful acetylenic derivatives of amines.

SUMMARY OF INVENTION

The compounds of the present invention may be represented by the following general Formula I:

Formula I

In the above general Formula I Z is β-methylthioethyl, β-benzylthioethyl, S-(5'-desoxyadenosin-5'-yl)-S-methylthioethyl, γ-guanidinopropyl, or

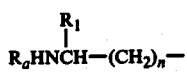

wherein n is the integer 2 or 3 and $R_1$ is hydrogen or a lower alkyl group of from 1 to 4 carbon atoms with the proviso that when $R_1$ is other than hydrogen, n is 2; and each of $R_a$ and $R_b$ is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched, or the group

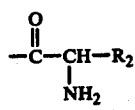

wherein $R_2$ is hydrogen, a straight or branched lower alkyl group of from 1 to 4 carbon atoms, benzyl or p-hydroxybenzyl; with the provisos that when Z is β-benzylthioethyl or S-(5'-desoxyadenosin-5'-yl)-S-methylthioethyl, $R_b$ is hydrogen and when Z is

each of $R_a$ and $R_b$ can be the same or different. Pharmaceutically acceptable salts and individual optical isomers of the compounds of general Formula I are also included within the scope of the present invention.

DETAILED DESCRIPTION OF INVENTION

In the above general Formula I in addition to the group

The symbol Z represents the substituent groups β-methylthioethyl, β-benzylthioethyl, S-(5'-desoxyadenosin-5'-yl)-β-methylthioethyl and γ-guanidinopropyl which are depicted by the following structures:

| | |
|---|---|
| 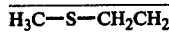 | β-methylthioethyl |
| 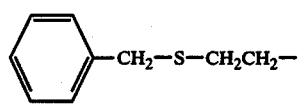 | β-benzylthioethyl |
| 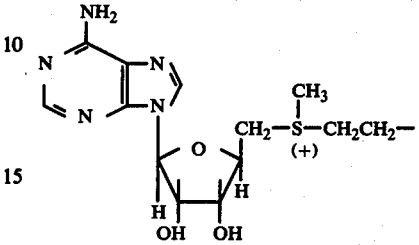 | S-(5'-desoxyadenosin-5-yl)-S-methylthioethyl |
|  | γ-guanidinopropyl |

As used in general Formula I the term alkylcarbonyl is taken to mean the group

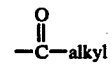

wherein the alkyl moiety has from 1 to 4 carbon atoms and is straight or branched, for example, methyl, ethyl, n-propyl, isopropyl. n-butyl, isobutyl and tert-butyl.

As used in general Formula I the term alkoxycarbonyl is taken to mean the group

wherein the alkoxy moiety, that is, -O-alkyl, has from 1 to 4 carbon atoms and is straight or branched, for example, methoxy, ethoxy, n-propoxy, isopropoxy, n-butoxy, and tert-butoxy.

Illustrative examples of straight or branched alkyl groups having from 1 to 4 carbon atoms as used in general Formula I are methyl, ethyl, n-propyl, n-butyl, isopropyl and tert-butyl.

Illustrative examples of pharmaceutically acceptable salts of the compounds of this invention include non-toxic acid addition salts formed with inorganic acids, such as, hydrochloric, hydrobromic, sulfuric and phosphoric acid, and organic acids, such as, methane sulfonic, salicylic, maleic, malonic, tartaric, citric, cyclamic and ascorbic acids.

Preferred compounds of this invention are those of general Formula I wherein Z is β-methylthioethyl, S-(5'-desoxyadenosin-5'-yl)-S-methylthioethyl, γ-guanidinopropyl or

and each R is hydrogen. More preferred compounds of this invention are those of general Formula I wherein Z is

with compounds wherein $R_1$ is hydrogen and n is 2 being most preferred.

Illustrative examples of compounds of the present invention are the following:

1-acetylene-3-methylthiopropylamine,
1-acetylene-3-benzylthiopropylamine,
1-acetylene-3-[S-(5'-desoxyadenosin-5'-yl)-S-(methyl)thio]-propylamine,
1-acetylene-4-guanidinobutylamine,
1-acetylene-1,4-butanediamine,
1-acetylene-1,5-pentanediamine,
N-(1-acetylene-4-aminobutyl)acetamide,
N-(1-acetylene-4-aminobutyl)propionamide,
N-(1-acetylene-3-methylthiopropyl)butyramide,
methyl N-(1-acetylene-4-aminobutyl)carbamate,
ethyl N-(1-acetylene-5-aminopentyl)carbamate,
isopropyl N-(1-acetylene-3-methylthiopropyl)carbamate,
1-acetylene-1,4-butylene-bis-tert-butyramide,
N-(1-acetylene-4-aminobutyl)-2-aminoacetamide,
N-(1-acetylene-5-aminopentyl)-2-aminodihydrocinnamide,
N-(1-acetylene-3-methylthiopropyl)-2-amino-p-hydroxydihydrocinnamide,
N-(1-acetylene-4-guanidinobutyl)-2-aminoacetamide,
1-acetylene-1,4-pentanediamine, and
1-acetylene-1,4-hexanediamine.

The compounds of general Formula I have many utilities. The compound of general Formula I wherein Z is β-benzylthioethyl, and $R_b$ is hydrogen is useful as an intermediate in the preparation of the corresponding pharmaceutically useful compound wherein Z is S-(5'-desoxyadenosin-5'-yl)-S-methylthioethyl.

The compounds of general Formula I wherein Z is other than β-benzylthioethyl are irreversible inhibitors of decarboxylase enzymes which are involved in polyamine formation rendering said compounds useful as pharmacological agents. Polyamines, particularly putrescine, spermidine and spermine are present in plant and animal tissues and in some microorganisms. Although the exact physiological role of polyamines has not been clearly delineated there is evidence to suggest that polyamines are involved with cell division and growth. (H. G. Williams-Ashman et al., The Italian J. Biochem. 25, 5–32 (1976), A. Raina and J. Janne, Med. Biol. 53, 121–147 (1975) and D. H. Russell, Life Sciences 13, 1635–1647 (1973)). Polyamines are essential growth factors for or involved in the growth processes of certain microorganisms, for example, E. coli, Enterobacter, Klebsiella, Staphylococcus aureus, C. cadaveris, Salmonella typhosa and Haemophilus parainfluenza. Polyamines are associated with both normal and neoplastic rapid growth there being an increase in the synthesis and accumulation of polyamines following a stimulus causing cellular proliferation. Also, levels of polyamines are known to be high in embryonic systems, the testes, in patients with rapidly growing tumors, leukemic cells and other rapidly growing tissues. It is known that there is a correlation between the activity of the decarboxylase enzymes of ornithine, S-adenosylmethionine, arginine and lysine and polyamine formation.

The biosyntheses of putrescine, spermidine and spermine are interrelated. Putrescine is the decarboxylation product of ornithine, catalyzed by ornithine decarboxylase. Putrescine formation may also occur by decarboxylation of arginine to form agmatine which is hydrolyzed to give putrescine and urea. Arginine is also involved in ornithine formation by action of the enzyme arginase. Activation of methionine by S-adenosylmethionine synthetase forms S-adenosylmethionine which is decarboxylated, afterwhich the propylamine moiety of activated methionine may be transferred to putrescine to form spermidine or the polyamine moiety may be transferred to spermidine to form spermine. Hence, putrescine serves as a precursor to spermidine and spermine and additionally has been shown to have a marked regulatory effect upon the polyamine biosynthetic pathway in that it has been shown that increased synthesis of putrescine is the first indication that a tissue will undergo renewed growth processes. Cadaverine which is the decarboxylation product of lysine has been shown to stimulate the activity of S-adenosylmethionine decarboxylase and is known to be essential to growth processes of many microorganisms, for example, H. parainfluenza.

The compounds of general Formula I wherein Z is

are irreversible inhibitors or ornithine decarboxylase and lysine decarboxylase respectively as n varies from 2 to 3. The compounds of general Formula I wherein Z is β-methylthioethyl or S-(5'-desoxyadenos in-5'-yl)-S-methylthioethyl are irreversible inhibitors of S-adenosylmethionine decarboxylase and wherein Z is γ-guanidinopropyl are irreversible inhibitors of arginine decarboxylase. As irreversible inhibitors of the above-enumerated decarboxylase enzymes the compounds of general Formula I wherein Z is other than β-benzylthioethyl are useful as antiinfective agents being effective in the control of microorganisms, for example, bacteria, fungi and viruses which are dependent upon polyamines for growth, for example, E. coli, Enterobacter, Klebsiella, Staphylococcus aureus, C. cadaveris, viruses such as, H. parainfluenza, picornaviruses, for example, encephalomyocarditis, herpes simplex, poxviruses and arboviruses, for example, Semliki forest. The compounds of general Formula I wherein Z is other than β-benzylthioethyl and

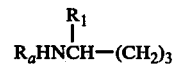

are also useful in the control of certain rapid growth processes, and can be used alone or in combination with one another. For example, the compounds are useful in the inhibition of spermatogenesis and embryogenesis and therefore the compounds find use as male antifertility agents and abortifacients. The compounds are also useful in the inhibition of the immune response, thus the compounds are useful as immunosuppressants for the treatment, for example, of myasthenia gravis, arthritis, multiple sclerosis and the prevention of tissue or organ transplant rejection, and are useful in the control of neoplastic growth, for example, solid tumors, leukemias and lymphomas. The compounds are also useful as inhibitors of abnormal cutaneous cell growth as found with a psoriatic condition.

The utility of compounds of general Formula I as irreversible inhibitors of ornithine or S-adenosylmethionine decarboxylases in vivo can be demonstrated as follows. An aqueous solution of an appropriate compound of Formula I is given orally or parenterally to male mice or rats. The animals are sacrificed 1 to 48 hours after administration of the compound and the ventral lobes of the prostate removed and homogenized with the activity of ornithine and S-adenosylmethionine decarboxylases being measured as generally described by E. A. Pegg and H. G. Williams-Ashman, Biochem. J. 108, 533–539 (1968) and J. Jänne and H. G. Williams-Ashman, Biochem. and Biophys. Res. Comm. 42, 222–228 (1971).

In administering the compounds of general Formula I wherein Z is

wherein n is 2 or 3 and $R_1$ is hydrogen it may be desirable to administer concurrently by known procedures a monoamine oxidase inhibitor such as trans(±)-2-phenylcycloproponamine or N-benzyl-N-methyl-2-propynylamine.

The compounds of general Formula I wherein Z is

wherein n is the integer 2 or 3 and $R_1$ is hydrogen are metabolic precursors of compounds of the following structure

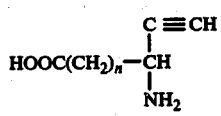

Formula II wherein n is the integer 2 or 3 which are known to be irreversible inhibitors of γ-aminobutyric acid transaminase and upon administration results in higher brain levels of γ-aminobutyric acid (GABA). As precursors of γ-acetylenic-γ-aminobutyric acid the above-described compounds of Formula I are useful in the treatment of disorders of the central nervous system consisting of involuntary movement associated with Huntington's chorea, Parkinsonism, extra-pyramidal effects of drugs, for example, neuroleptic siezure disorders associated with epilepsy, alcohol withdrawal, barbiturate withdrawal, psychoses associated with schizophrenia, depression, manic depression and hyperkinesis.

Several previous studies have shown that γ-aminobutyric acid is a major inhibitory transmitter of the central nervous system as reported, for example, by Y. Godin et al., Journal Neurochemistry, 16, 869 (1969) and that disturbance of the excitation and inhibition interplay can lead to diseased states such as Huntington's chorea (The Lancet, Nov. 9, 1974, pp. 1122–1123) Parkinsonism, schizophrenia, epilepsy, depression, hyperkinesis and manic depression disorders, Biochem, Pharmacol. 23, 2637–2649 (1974).

That the compounds of general Formula I wherein Z is

wherein n is 2 or 3 and $R_1$ is hydrogen are converted metabolically to the compounds of Formula II may be demonstrated by the protective effect of the compounds on audiogenic seizures in mice of the DBA strain measured by the general method described by Simler et al., Biochem. Pharmacol. 22, 1701 (1973) which is currently used to evidence antiepileptic activity.

The compounds of general Formula I wherein $R_b$ is hydrogen are useful as chemical intermediates for the preparation of novel cephalosporin derivatives which are useful as antibiotics and have the following general structure:

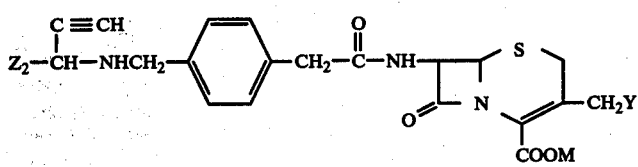

Formula III wherein $Z_2$ is β-methylthioethyl, β-benzylthioethyl, S-(5'-desoxyadenosin-5'-yl)-S-methylthioethyl, γ-guanidinopropyl or $$R_aHNCH-(CH_2)_n-$$
$$|$$
$$R_1$$

wherein n is 2 or 3, $R_1$ is hydrogen or lower alkyl of from 1 to 4 carbon atoms and $R_a$ is hydrogen; M is hydrogen or a negative charge; and Y is hydrogen or acetoxy.

The compounds of general Formula III and the pharmaceutically acceptable salts and individual optical isomers thereof are novel compounds useful as antibiotics and can be administered in a manner similar to that of many well known cephalosporin derivatives, for example, cephalexin, cephalothin, or cephaloglycine. The compounds of general Formula III and pharmaceutically acceptable salts and isomers thereof can be administered alone or in the form of pharmaceutical preparations either orally or parenterally and topically to warm blooded animals, that is, birds and mammals, for example, cats, dogs, bovine cows, sheep, horses and humans. For oral administration the compounds can be administered in the form of tablets, capsules or pills or in the form of elixirs or suspensions. For parenteral administration, the compounds may best be used in the form of a sterile aqueous solution which may contain other solutes, for example, enough saline or glucose to make the solution isotonic. For topical administration the compounds of general Formula III, salts and isomers thereof may be incorporated into creams or ointments.

Illustrative examples of bacteria against which the compounds of general Formula III and the pharmaceutically acceptable salts and individual optical isomers thereof are active *Staphylococcus aureus, Salmonella schotmuehleri, Klebsiella pneumoniae, Diplococcus pneumoniae* and *Streptococcus pyogenes.*

Illustrative pharmaceutically acceptable non-toxic inorganic acid addition salts of the compounds of general Formula III are mineral acid addition salts, for example, hydrogen chloride, hydrogen bromide, sulfates, sulfamates, phosphate, and organic acid addition salts are, for example, maleate, acetate, citrate, oxalate, succinate, benzoate, tartrate, fumarate, malate and ascorbate. The salts can be formed by conventional means.

Illustrative examples of compounds of general Formula III are 7-[[2-[4-(1-acetylene-4-aminobutylaminomethyl)phenyl]acetyl]amino]-3-acetyloxymethyl-8-oxo-5-thia-1-azabicyclo[4.2.0]oct-2-ene-2-carboxylic acid; 7-[[2-[4-(1-acetylene-3-methyl-thiopropylaminomethyl)-phenyl]acetyl]amino]-3-acetyloxymethyl-8-oxo-5-thia-1-azabicyclo[4.2.0]oct-2-ene-2-carboxylic acid and 7-[[2-[4-(1-acetylene-5-aminopentylaminomethyl)phenyl]acetyl]-amino]-3-acetyloxymethyl-8-oxo-5-thia-1-azabicyclo[4.2.0]-oct-2-ene-2-carboxylic acid.

The preparation of the compounds of general Formula III is described hereinbelow.

As pharmacologically useful agents the compounds of general Formula I wherein Z is other than β-benzyl-thioethyl can be administered in various manners to the patient being treated to achieve the desired effect. The compounds can be administered alone or in the form of a pharmaceutical preparation orally, parenterally, for example, intravenously, intraperitoneally, or subcutaneously, or topically. The amount of compound administered will vary over a wide range and can be any effective amount. Depending on the patient to be treated, the condition being treated and the mode of administration, the effective amount of compound administered will vary from about 0.1 mg/kg to 500 mg/kg of body weight of the patient per unit dose and preferably will be about 10 mg/kg to about 100 mg/kg of body weight of patient per unit dose. For example, a typical unit dosage form may be a tablet containing from 10 to 300 mg of a compound of Formula I which may be administered to the patient being treated 1 to 4 times daily to achieve the desired effect.

As used herein the term patient is taken to mean warm blooded animals such as mammals, for example, cats, dogs, rats, mice, guinea pigs, horses, bovine cows, sheep and humans.

The solid unit dosage forms can be of the conventional type. Thus, the solid form can be a capsule which can be of the ordinary gelatin type containing a novel compound of this invention and a carrier, for example, lubricant and inert fillers such as lactose, sucrose and corn starch. In another embodiment, the novel compounds are tableted with conventional tablet bases such as lactose, sucrose or corn starch in combination with binders such as acacia, corn starch or gelatin, disintegrating agents such as corn starch, potato starch, or alginic acid, and a lubricant such as stearic acid, or magnesium stearate.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable or synthetic origin, for example, peanut oil, soybean oil, and mineral oil. In general, water, saline, aqueous dextrose, and related sugar solutions, ethanols and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

The compounds of general Formula I wherein Z is β-methylthioethyl, β-benzylthioethyl, or

and each of $R_a$ and $R_b$ is hydrogen are prepared by treating a suitably protected propargylamine derivative with a strong base to form a protected propargylamine carbanion intermediate which is reacted with an alkylating reagent of the formula $R_3X$ wherein X is halogen, for example, chlorine or bromine, and $R_3$ is β-methylthioethyl, β-benzylthioethyl or

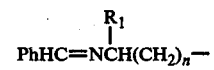

wherein n is the integer 2 or 3, and $R_1$ is hydrogen or a lower alkyl of from 1 to 4 carbon atoms, and subsequently removing the protecting groups by hydrolysis as represented by the following reaction scheme:

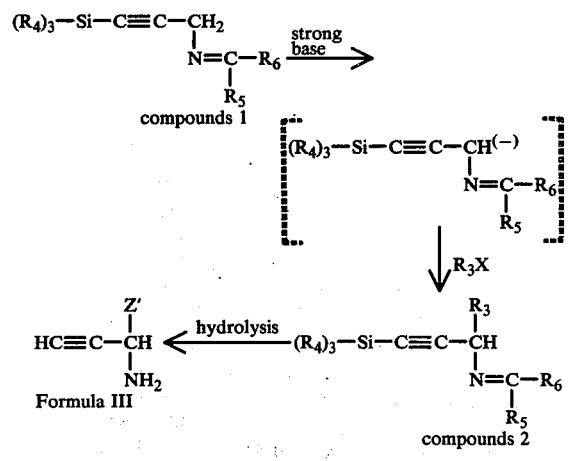

In the above reaction scheme $R_3$ and X have the meanings defined hereinabove; Ph represents phenyl; $R_5$ is hydrogen, methoxy or ethoxy; $R_6$ is phenyl, tert-butyl, triethylmethyl, 1-adamantanyl, or 2-furyl with the proviso that when $R_5$ is hydrogen, $R_6$ is not 1-adamantanyl or 2-furyl; $R_4$ is a straight or branched lower alkyl group having from 1 to 4 carbon atoms, such as methyl, ethyl, n-propyl and tert-butyl; and Z' is β-methylthioethyl, β-benzylthioethyl

wherein n is the integer 2 or 3.

Suitable strong bases which may be employed in the above reaction to form the carbanion are those which will abstract a proton from the carbon atom adjacent to the acetylene moiety, such as, alkyl lithium, for example, butyl lithium or phenyl lithium, lithium di-alkylamide, for example, lithium diisopropylamide, lithium amide, tertiary potassium butylate or sodium amide.

The alkylating reagents, $R_3X$, employed in the above reaction are known in the art or can be prepared by methods known in the art. The reactant

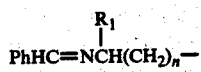

wherein $R_1$ is hydrogen can be prepared, for example, by reacting 3-bromo-n-propylamine hydrochloride or 4-bromo-n-butylamine hydrochloride with benzaldehyde and an organic amine, such as, a trialkylamine, for example, triethylamine in a solvent such as an ether, for example, diethyl ether, tetrahydrofuran or dioxane, chloroform or dichloromethane. The reactant

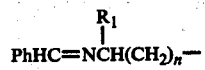

wherein $R_1$ is a lower alkyl group of from 1 to 4 carbon atoms and n is the integer 2 are prepared by reacting an appropriate γ-aminoalkylbromide hydrobromide of the formula

with benzaldehyde and an organic amine such as triethylamine. The γ-aminoalkylbromide hydrobromide is prepared from the corresponding γ-aminoalkanol by treatment with hydrogen bromide. The γ-aminoalkanol derivative is obtained by treating an appropriate β-ketoalkanoic acid ester of the formula

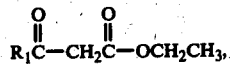

wherein $R_1$ is a lower alkyl group of from 1 to 4 carbon atoms, with hydroxylamine hydrochloride and reducing the resulting oxime by lithium aluminum hydride reduction.

The alkylating reaction may be carried out in an aprotic solvent, for example, benzene, toluene, ethers, tetrahydrofuran, dimethylsulfoxide, hexamethyl phosphortriamide. The reaction temperature varies from about −100° to 25° C. preferably about −70° C. and the reaction time varies from about ½ hour to 24 hours.

Removal of the protecting groups, as represented in the reaction scheme in the step going from compounds 2 to compounds of formula III, is achieved by treatment with aqueous acid, for example, hydrochloric acid followed by aqueous base, for example, sodium hydroxide or potassium or treatment with phenylhydrazine, hydroxylamine or hydrazine then with aqueous base.

The propargylamine derivatives, that is, compounds 1, wherein $R_5$ is hydrogen are prepared by the addition of protecting groups on the acetylene function and the nitrogen function of propargylamine. Protection of the nitrogen function of the propargylamine is accomplished by forming in a known manner a Schiff's base with a non-enolizable carbonyl bearing compound selected from benzaldehyde, 2,2-dimethylpropanal and 2,2-diethylbutanal.

Protection of the acetylenic function is accomplished by reacting the above-described Schiff's base with a trialkylsilyl chloride wherein the alkyl moiety has from 1 to 4 carbon atoms and is straight or branched, for example, trimethylsilylchloride or triethylsilylchloride forming in a known manner the corresponding trialkylsilyl derivative.

The propargylamine derivatives, compounds 1, wherein $R_5$ is methoxy or ethoxy are prepared by reacting propargylamine wherein the acetylene function is protected by a trialkylsilyl group, wherein the alkyl moiety has from 1 to 4 carbon atoms and is straight or branched, with benzoyl chloride, pivalic acid chloride, or 2,2-diethylbutyric acid chloride, 2-furoic acid chloride or 1-adamantane carboxylic acid chloride at 0° C. in diethyl ether, dioxane, tetrahydrofuran, chloroform, methylenechloride, dimethylformamide, dimethylacetamide, or chlorobenzene in the presence of an organic base such as triethylamine or pyridine after which the reaction mixture is allowed to warm to about 25° C. for one hour. The resulting amide derivative is combined with an alkylating reagent, such as, methylfluorosulfonate, dimethylsulfate, methyliodide, methyl p-toluenesulfonate or trimethyloxonium hexafluorophosphate when $R_5$ is methoxy or triethyloxonium tetrafluoroborate when $R_5$ is ethoxy at about 25° C. in a chlorinated hydrocarbon solvent such as methylene chloride, chlorobenzene or chloroform, and the reaction mixture is refluxed for about 12 to 20 hours. The mixture is then cooled to about 25° C. and an organic base such as triethylamine or pyridine is added, after which the solution is extracted with brine and the product isolated.

The protected propargylamine starting material is obtained by treating a 3-trialkylsilylprop-2-ynyl-1-iminobenzyl derivative, that is compounds 1, wherein $R_5$ is hydrogen and $R_6$ is phenyl with hydrazine or phenylhydrazine at about 25° C. for about ½ hour after which the mixture is diluted with, for example, petroleum ether, benzene or toluene and the iminobenzyl derivative isolated. Alternatively the imine is hydrolyzed with 0.5 to 1 N HCl, and the aqueous phase evaporated to afford the amine hydrochloride.

The compounds of general Formula I wherein Z is γ-guanidinopropyl are prepared from the corresponding derivative wherein Z is

wherein $R_1$ is hydrogen, and n is 2 and wherein $R_a$ is hydrogen, that is, the compound

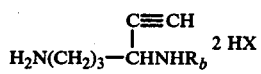

Compounds 3 wherein X is halogen, for example, chlorine and $R_b$ has the meaning defined in Formula I with the proviso that any free amino group is suitably protected with, for example, benzyloxycarbonyl by treatment with an alkylisothiouronium salt, for example, ethylisothiouronium hydrobromide by procedures generally known in the art; for example, Organic Synthesis, III, p. 440 (1955). The reaction is carried out in the presence of a base, such as aqueous sodium hydroxide or potassium hydroxide at a pH of about 10 at a temperature of about 25° C. for about 6 to 60 hours after which the reaction mixture is neutralized with concentrated hydrochloric acid and the product isolated. When appropriate, protecting groups are removed by acid hydrolysis, for example, by treatment with HBr in dioxane. The preparation of compounds 3 is described hereinbelow.

The compounds of Formula I wherein Z is S-(5'-desoxyadenosin-5'-yl)-S-methylthioethyl and $R_6$ is hydrogen are prepared by treating for about one hour the corresponding compound wherein Z is β-benzylthioethyl, that is, the compound

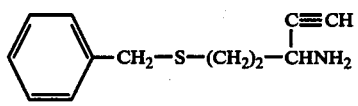

Compound 4 with sodium amide or lithium amide in liquid ammonia followed by the addition of finely divided sodium or lithium metal until the blue color persists, and reacting the thus obtained di-metal salt with the 5-p-toluenesulfonyl-, 5-bromo- or 5-chloro derivative of 2',3'-isopropylidene adenosine having the structure

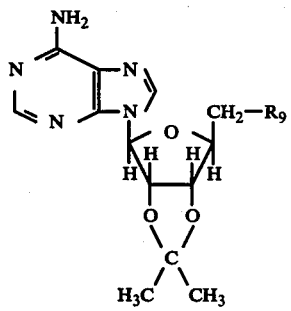

Compound 5 wherein $R_9$ is p-toluenesulfonyl, chlorine or bromine for about two hours in liquid ammonia followed by acid hydrolysis and treatment with methyl iodide in acidic solvents such as formic acid, acetic acid, trifluoroacetic acid or trichloroacetic acid.

Following is described the preparation of compounds of general Formula I, other than compounds wherein Z is γ-guanidinopropyl, wherein $R_a$ and/or $R_b$ are other than hydrogen, that is, compounds of general Formula I wherein Z is β-methylthioethyl and $R_b$ is other than hydrogen and compounds wherein Z is

wherein either or both of $R_a$ and $R_b$ is other than hydrogen including Compounds 3. The following description is applicable to all the above said compounds, however, in preparing compounds wherein Z is

it is necessary to protect one or the other of the amino groups prior to treatment with the appropriate reactant, that is, acid halide or anhydride, alkyl haloformate or acid of the formula

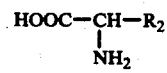

or anhydride thereof as described below to give compounds wherein either or both of $R_a$ and $R_b$ is other than hydrogen as follows: When $R_a$ is hydrogen and $R_b$ is other than hydrogen, the amino group to which $R_a$ is attached is protected as a phthalimido derivative by treating the corresponding derivative wherein $R_a$ is hydrogen with a carbalkoxyphthalimide wherein the alkoxy moiety has from 1 to 4 carbon atoms, for example, carbethoxyphthalimide in a solvent such as an ether or a lower alcohol, such as, methanol, for ½ to 3 hours at about 0° to 50° C. followed by extraction with acid, for example, hydrochloric acid prior to treatment with the appropriate reactant described below to give compounds wherein $R_b$ is other than hydrogen. The phthalimide group is subsequently removed by treatment with hydrazine in a lower alcohol solvent, such as, methanol at about 50° to 100° C. for about 1 to 4 hours. The thus obtained compounds, that is, compounds wherein $R_a$ is hydrogen and $R_b$ is other than hydrogen may be treated with the appropriate reactants described below to give compounds wherein $R_a$ and $R_b$ are both other than hydrogen and may be the same or different. In preparing compounds wherein $R_a$ is other than hydrogen and $R_b$ is hydrogen the amino group to which $R_b$ is attached is protected with, for example, a benzyloxycarbonyl group by treatment of the corresponding derivative wherein $R_b$ is hydrogen with a benzyl haloformate, such as, benzyl chloroformate prior to treatment with the appropriate reactant described below to give compounds wherein $R_a$ is other than hydrogen. The benzyloxy group is subsequently removed by acid hydrolysis, for example, by treatment with HBr in dioxane.

The compounds of general Formula I wherein $R_a$ or $R_b$ is alkylcarbonyl wherein the alkyl moiety is straight or branched and has from 1 to 4 carbon atoms are prepared by treating the corresponding derivatives wherein $R_a$ or $R_b$ is hydrogen or is suitably protected or $R_b$ is other than hydrogen as described hereinabove with an acid halide of the formula

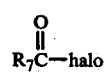

wherein halo is a halogen atom, for example, chlorine or bromine and $R_7$ is a straight or branched alkyl group having from 1 to 4 carbon atoms or an appropriate acid anhydride, in water in the presence of a base such as sodium hydroxide or sodium borate at a temperature of about 0° to 25° C. for about ½ hour to 6 hours. When appropriate, protecting groups are removed as described hereinabove by treatment with hydrazine or acid.

The compounds of general Formula I wherein $R_a$ or $R_b$ is alkoxycarbonyl wherein the alkoxy moiety is straight or branched and has from 1 to 4 carbon atoms are prepared by treating the corresponding derivative wherein $R_a$ or $R_b$ is hydrogen or is suitably protected or $R_b$ is other than hydrogen as described hereinabove with an alkyl haloformate of the formula

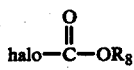

wherein halo is a halogen atom such as chlorine or bromine and $R_8$ is a straight or branched alkyl group having from 1 to 4 carbon atoms in water in the presence of a base such as sodium hydroxide or sodium borate at a temperature of about 0° to 25° C. for about ½ hour to 6 hours when appropriate protecting groups are removed as described hereinabove by treatment with hydrazine or acid.

The compounds of general Formula I wherein $R_a$ or $R_b$ is

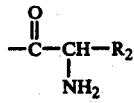

wherein $R_2$ is hydrogen, a straight or branched lower alkyl group of from 1 to 4 carbon atoms, benzyl or p-hydroxybenzyl are prepared by treating the corresponding derivative wherein $R_a$ or $R_b$ is hydrogen or is suitably protected or $R_b$ is other than hydrogen as described hereinabove with an acid of the formula

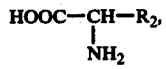

or an anhydride thereof, wherein the amino group is protected with a suitable blocking group such as benzyloxycarbonyl or tert-butoxycarbonyl and $R_2$ has the meaning defined hereinabove in an ether, such as, tetrahydrofuran or dioxane, methylene chloride or chloroform and in the presence of a dehydrating agent, such as, dicyclohexylcarbodiimide when the free acid is employed, at a temperature of about 0° to 35° C. for about 1 to 12 hours followed by acid and base hydrolysis and when appropriate treatment with hydrazine to remove the protecting groups.

Alternatively the compound of general Formula I where Z is

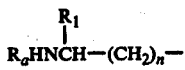

wherein n is 2, $R_1$ is hydrogen and each of $R_a$ and $R_b$ is hydrogen may be prepared as follows. To n-butyllithium (50 ml of a 2.0 M solution, 0.1 M) is added 21.5 g (0.1 M) of 3-trimethylsilylprop-2-ynyl-1-iminobenzyl in 1 liter of tetrahydrofuran at −78° C. after which 15.7 g (0.1 M) of bromochloropropane is added and the solution maintained at −30° C. for 2 hours. The reaction mixture is then treated with water and extracted with ether. The ether extract is evaporated leaving a residue which is taken up in 100 ml of dimethylformamide (DMF) containing 18.5 g (0.1 M) of potassium phthalimide and heated at 100° C. for 3 hours. The DMF is removed under reduced pressure (12 mm) and the residue is taken up in ether, washed with water, dried over magnesium sulfate and evaporated. The oily residue in 300 ml of ethanol is treated with 10 g (0.2 M) of hydrazine hydrate at reflux overnight after which the solvent is evaporated leaving a residue which is treated with an aqueous base, extracted with an organic solvent and evaporated leaving a residue which is heated with 200 ml of 6 N HCl for about 10 to 48 hours. The aqueous solution is extracted with methylene chloride, made alkaline and re-extracted with methylene chloride. The organic solution is concentrated and the residue distilled to afford the product, that is, 1-acetylene-1,4-butanediamine, b.p. 50° C./0.4 mm.

The individual optical isomers of compounds of Formula I wherein each of $R_a$ and $R_b$ is H may be resolved by protecting the amine distal to the acetylene as a phthalimido derivative using carbalkoxyphthalimidate, wherein the alkoxy moiety is, for example, a straight or branched lower alkoxy group having from 1 to 4 carbon atoms, in an ether or lower alcohol and using a (+) or (−) binaphthylphosphoric acid salt by the method of R. Viterbo et al., Tetrahedron Letters 48, 4617 (1971) or using (−) camphor-10-sulfonic acid followed by treatment with hydrazine. Individual optical isomers of compounds wherein each of $R_a$ and $R_b$ is other than H may be obtained as described herein for the racemate only starting with the resolved amine or the resolved phthalimido derivative.

The compounds of general Formula III are prepared by reacting a compound of the formula

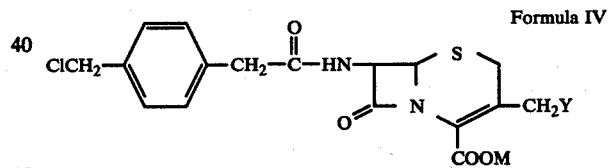

Formula IV wherein Y and M have the meanings defined in general Formula III, which compounds are prepared as described in U.S. Pat. No. 3,919,206 which patent is incorporated herein by reference thereto, with a compound of general Formula I wherein each of $R_a$ and $R_b$ is hydrogen and the amino group distal to the acetylene function is protected with a suitable blocking group such as tert-butoxycarbonyl. The reaction is generally carried out in a solvent, such as, a lower alcohol, for example, methanol, ethanol or isopropyl alcohol, or dimethylsulfoxide, dimethylformamide or aqueous mixtures of these solvents. The temperature of the reaction may vary from about 0° to 125° C. and the reaction time may vary from about ½ hour to 24 hours. Following the solvolysis reaction the amino protecting group is removed by acid hydrolysis, and the cephalosporin products are isolated by conventional procedures.

The following Example 1 illustrates the use of a compound of general Formula I wherein $R_a$ and $R_b$ are hydrogen as a chemical intermediate in the preparation of a cephalosporin of Formula III.

EXAMPLE 1

7-[[2-[4-(1-acetylene-4-aminobutylaminomethyl)-phenyl]acetyl]amino]-3-acetyloxymethyl-8-oxo-5-thia-1-azabicyclo[4.2.0]oct-2-ene-2-carboxylic acid A mixture of 1 g of 3-acetyloxymethyl-7-[[2-[4-(chloromethyl)phenyl]acetyl]amino]-8-oxo-5-thia-1-azabicyclo[4.2.0]oct-2-ene-2-carboxylic acid and 1 g of 1-acetylene-1,4-butanediamine wherein the amino group distal to the acetylene function is protected with tert-butoxycarbonyl in 50 ml of ethanol was stirred at 25° C. for 24 hours after which the solvent is removed leaving a residue which is treated with mild acid and chromatographed on silica gel using benzene-acetone as the eluant to give 7-[[2-[4-(1-acetylene-4-aminobutylaminomethyl)phenyl]-acetyl]amino]-3-acetyloxymethyl-8-oxo-5-thia-1-azabicyclo[4.2.0]oct-2-ene-2-carboxylic acid.

EXAMPLE 2

An illustrative composition for hard gelatin capsules is as follows:

| (a) | 1-acetylene-1,4-butanediamine | 20 mg |
| --- | --- | --- |
| (b) | talc | 5 mg |
| (c) | lactose | 90 mg |

The formulation is prepared by passing the dry powders of (a) and (b) through a fine mesh screen and mixing them well. The powder is then filled into hard gelatin capsules at a net fill of 115 mg per capsule.

EXAMPLE 3

An illustrative composition for tablets is as follows:

| (a) | 1-acetylene-1,4-pentanediamine | 20 mg |
| --- | --- | --- |
| (b) | starch | 43 mg |
| (c) | lactose | 45 mg |
| (d) | magnesium stearate | 2 mg |

The granulation obtained upon mixing the lactose with the compound (a) and part of the starch and granulated with starch paste is dried, screened, and mixed with the magnesium stearate. The mixture is compressed into tablets weighing 110 mg each.

EXAMPLE 4

An illustrative composition for an injectable suspension is the following 1 ml ampul for an intramuscular injection.

| | | Weight percent |
| --- | --- | --- |
| (a) | 1-acetylene-3-methylthiopropylamine | 1.0 |
| (b) | polyvinylpyrrolidone | 0.5 |
| (c) | lecithin | 0.25 |
| (d) | water for injection to make | 100.0 |

The materials (a)-(d) are mixed, homogenized and filled into 1 ml ampuls which are sealed and autoclaved 20 minutes at 121° C. Each ampul contains 10 mg per ml of novel compound (a).

The following examples further illustrate the compounds of the invention.

EXAMPLE 5

1-Acetylene-1,4-butanediamine

To 10.8 g (0.05 M) of 3-trimethylsilylprop-2-ynyl-1-iminobenzyl in 500 ml of tetrahydrofuran under nitrogen atmosphere at −78° C. is added n-butyllithium (0.05 M). After 10 minutes the dark red carbanion is treated with 11.3 g (0.05 M) of 3-bromopropyl-1-iminobenzyl in 20 ml of tetrahydrofuran. After 3 hours at −78° C. 50 ml of water is added and the tetrahydrofuran is evaporated leaving a residue which is heated at reflux under nitrogen atmosphere with 100 ml of 6 N hydrochloric acid for 48 hours. Upon cooling the aqueous solution is washed with methylene chloride, made alkaline with aqueous sodium hydroxide and re-extracted with methylene chloride. The methylene chloride extract is dried over magnesium sulfate, filtered, concentrated and distilled to afford 1-acetylene-1,4-butanediamine, b.p. 50° C./0.4 mm.

The dicyclamate salt of 1-acetylene-1,4-butanediamine is prepared by dissolving the diamine in methanol then adding a 2 mole equivalent of cyclamic acid. The solution is concentrated after which ether is added and the resulting precipitate, dicyclamate salt of 1-acetylene-1,4-butanediamine collected. The dihydrochloride is made by treating the diamine with aqueous hydrochloric acid followed by evaporization and recrystallization from methanol, M.P. 173° C.

EXAMPLE 6

3-Bromopropyl-1-iminobenzyl

The 3-bromopropyl-1-iminobenzyl derivative employed in Example 5 is obtained from 43.6 g (0.2 M) of 3-bromopropylamine hydrobromide in 300 ml of methylene chloride to which is added 21.2 g (0.2 M) of benzaldehyde and 20.2 g (0.2 M) of triethylamine. The mixture is stirred at room temperature overnight after which the solvent is removed on a rotorvap and the residue treated with ether. The ether solution is filtered, and the filtrate dried over magnesium sulfate, filtered, concentrated and distilled to afford 3-bromopropyl-1-iminobenzyl, b.p. 110° C./0.5 mm.

EXAMPLE 7

1-Acetylene-3-benzylthiopropylamine

A solution of 21.5 g (0.1 M) of 3-trimethylsilylprop-2-ynyl-1-iminobenzyl in 400 ml of tetrahydrofuran at −78° C. is treated with n-butyllithium (50 ml of a 2.0 M solution, 0.1 M) after which 18.6 g (0.1 M) of S-benzyl-2-chloroethanthiol in 20 ml of tetrahydrofuran is added and the solution is maintained at −30° C. for 15 hours. The mixture is treated with brine, extracted with ether, and the ether extract evaporated leaving a residue which is treated with 400 ml of a 2 M solution of aqueous hydrochloric acid and refluxed for 12 hours. The aqueous solution is washed well with methylene chloride, made alkaline using potassium carbonate and re-extracted. The organic solution is dried over magnesium sulfate, filtered and the filtrate concentrated. The resulting residue is distilled under high vacuum to give 1-acetylene-3-benzylthiopropylamine which is purified as the hydrochloride.

EXAMPLE 8

1-Acetylene-3-methylthiopropylamine

When in the procedure of Example 7 an appropriate amount of S-methyl-2-chloroethanthiol is substituted for S-benzyl-2-chloroethanthiol, 1-acetylene-3-methylthiopropylamine is obtained.

EXAMPLE 9

5'-Desoxy-5'-[S-(3-acetylene-3-aminopropyl)-S-(methyl)-thio]adenosine

To 10 mM of sodium amide in 200 ml of ammonia is added 10 mM of 1-acetylene-3-benzylthiopropylamine, prepared in Example 7. After 1 hour sodium metal in small pieces is added until the blue color persists for 5 minutes then 10 mM of 2',3'-isopropylidene-5'-p-toluene-sulfonyl adenosine is added. After 2 hours the ammonia is allowed to evaporate, and the remaining residue is treated with 1 N sulfuric acid for 48 hours at 25° C. after which the pH is adjusted to 6 and the solution is applied to an ion exchange resin, KV-2NH$_4$$^+$ and then a DEAE cellulose (OH$^-$) column. The aqueous eluate is evaporated and the residue recrystallized from water/ethanol to give 5'-desoxy-5'-(3-acetylene-3-aminopropylthio)adenosine. The adenosine derivative is dissolved in a mixture of 4 ml of acetic acid and 4 ml of formic acid after which 1 ml of methyliodide is added. The mixture is maintained under a nitrogen atmosphere for 6 days at 25° C. then the solvents are removed under reduced pressure at 25° C. The resulting residue is dissolved in 8 ml of 0.1 N HCl, and a saturated solution of Reinecke salt is added. The resulting precipitate is collected and treated with 1.5 g of silver sulfate in acetone at 25° C. for 36 hours. The insoluble residue is filtered off and washed with methanol. The combined filtrates are concentrated under reduced pressure to yield 5'-desoxy-5'-[S-(3-acetylene-3-aminopropyl)-S-(methyl)thio]adenosine.

EXAMPLE 10

N-(1-Acetylene-4-guanidinobutyl)acetamide

To a solution of 1.54 g (10 mM) of N-(1-acetylene-4-aminobutyl)acetamide in 10 ml of methanol and 10 ml of water is added 3.7 g (20 mM) of ethylisothiouronium hydrobromide. The pH of the solution is maintained at 10 by the addition of 2 M sodium hydroxide solution during 48 hours at 25° C. after which the methanol is evaporated and the aqueous solution extracted well with dichloromethane. The organic phase is dried and evaporated to afford N-(1-acetylene-4-guanidinobutyl)acetamide.

When in the above procedure an appropriate amount of benzyl N-(1-acetylene-4-aminobutyl)carbamate is substituted for N-(1-acetylene-4-aminobutyl)acetamide, benzyl N-(1-acetylene-4-guanidinobutyl)carbamate is obtained which is treated with HBr in dioxane (20 ml of a 40% (w/w) solution) for 30 minutes at 28° C. after which ether is added and the precipitated 1-acetylene-4-guanidinobutylamine collected.

EXAMPLE 11

N-(4-Acetylene-4-aminobutyl)-2-aminopropionamide

A solution of 492 mg (2 mM) of N-(1-acetylene-4-aminobutyl)benzyl carbamate in 4 ml of dichloromethane is treated with 446 mg (2 mM) of N-carbobenzoxyalanine and 412 mg (2 mM) of N,N'-dicyclohexylcarbodiimide for about 15 hours at 25° C. after which the solution is cooled to 0° C. and the precipitated dicyclohexylurea filtered off. The filtrate is diluted with 20 ml of dichloromethane and washed with 1 N hydrochloric acid, water and aqueous sodium bicarbonate, then dried and concentrated. The resulting residue is treated with 6 ml of a 40% (w/w) solution of hydrogen bromide in dioxane at 25° C. for 30 minutes then diluted with ether and the precipitated N-(4-acetylene-4-aminobutyl)-2-aminopropionamide dihydrobromide collected.

EXAMPLE 12

N-(4-Acetylene-4-aminobutyl)acetamide hydrobromide

A solution of 492 mg (2 mM) of N-(1-acetylene-4-aminobutyl)-benzyl carbamate in 10 ml of chloroform is treated with 202 mg (2 mM) of triethylamine followed by 160 mg (2.1 mM) of acetyl chloride. After 1 hour at 25° C. the solution is washed with water, dilute hydrochloric acid, and aqueous sodium carbonate, then dried and concentrated. The resulting residue is treated with 6 ml of a 40% (w/w) solution of hydrogen bromide in dioxane for 30 minutes at 25° C., then ether is added on the precipitated N-(4-acetylene-4-aminobutyl)acetamide hydrobromide is collected.

When in the above procedure an appropriate amount of ethyl chloroformate is substituted for acetyl chloride, N-(4-acetylene-4-aminobutyl)-ethyl carbamate is obtained.

EXAMPLE 13

N-(1-Acetylene-4-aminobutyl)acetamide

A solution of 242 mg (1 mM) of N-(4-acetylene-4-aminobutyl)phthalimide in 10 ml of chloroform is treated with 1 ml of triethylamine followed by 78 mg (1 mM) of acetyl chloride in 5 ml of chloroform. After 1 hour at 25° C. the solution is washed with water, dried and concentrated. The resulting residue is dissolved in 10 ml of ethanol and treated with 60 mg (1.1 mM) of hydrazine hydrate at reflux for 2 hours after which the solvent is evaporated. The residue is treated with 1 N sodium hydroxide solution until the solid dissolves then is extracted with dichloromethane. The organic phase is dried and concentrated to give N-(1-acetylene-4-aminobutyl)acetamide.

N-(4-Acetylene-4-aminobutyl)phthalimide used in the above procedure is prepared as follows. A solution of 13.5 g (61.6 mM) of carbethoxyphthalimide in 70 ml of tetrahydrofuran is added dropwise to a solution of 6.91 g (61.6 mM) of 1-acetylene-1,4-butanediamine in 30 ml of tetrahydrofuran in an ice-bath. After completion of the addition the mixture is stirred for 2 hours at 25° C. then diluted with ether, and the solution is extracted with 1 N hydrochloric acid (3 × 100 ml). The aqueous phase is washed several times with ether then concentrated to dryness leaving a residue which is recrystallized from ethanol to give N-(4-acetylene-4-aminobutyl)phthalimide HCl which is converted to the free base by known procedures.

When in the procedure of Example 13 an appropriate amount of ethyl chloroformate is used in place of acetyl chloride, N-(1-acetylene-4-aminobutyl)-ethyl carbamate is obtained.

When in the procedure of Example 13 an appropriate amount of benzyl chloroformate is substituted for acetyl chloride, N-(1-acetylene-4-aminobutyl)-benzyl carbamate is obtained.

EXAMPLE 14

N-(1-Acetylene-4-aminobutyl)-2-aminopropionamide

A solution of 450 mg (2 mM) of N-carbobenzoxyalanine in 10 ml of dichloromethane is treated with 202 mg (2 mM) of triethylamine followed by 218 mg (2 mM) of ethyl chloroformate. After 1 hour at 25° C. the solution is treated with 484 mg (2 mM) of N-(4-acetylene-4-aminobutyl)phthalimide in 10 ml of chloroform and maintained at 25° C. for one hour after which the solution is washed with 1 N hydrochloric acid, water and aqueous sodium carbonate then dried and concentrated. The residue is dissolved in 15 ml of ethanol and treated with 100 mg (2 mM) of hydrazine hydrate at reflux for 2 hours after which the solvent is evaporated. The residue is treated with 5% aqueous sodium hydroxide and extracted with dichloromethane. The organic phase is dried and concentrated and the resulting residue is treated with 5 ml of a 40% (w/w) solution of hydrogen bromide in dioxane. After 30 minutes at 25° C. the mixture is treated with ether and the precipitated N-(1-acetylene-4-aminobutyl)-2-aminopropionamide dihydrobromide collected.

EXAMPLE 15

1-Acetylene-1,4-butylene-bis-2-aminopropionamide

A solution of 900 mg (4 mM) of N-carbobenzoxyalanine in 10 ml of dichloromethane is treated with 405 mg (4 mM) of triethylamine followed by 435 mg (4 mM) of ethyl chloroformate. After 1 hour at 25° C. the solution is treated with 224 mg (2 mM) of 1-acetylene-1,4-butanediamine in 5 ml of dichloromethane. The solution is maintained at 25° C. for 1 hour then is washed with water, dried and concentrated. The resulting residue is treated with 6 ml of a 40% (w/w) solution of hydrogen bromide in dioxane for 30 minutes at 25° C. then diluted with ether. The precipitate is collected to afford 1-acetylene-1,4-butylene-bis-2-aminopropionamide dihydrobromide.

EXAMPLE 16

1-Acetylene-1,4-butylene-bis-acetamide

A solution of 0.5 g (4.5 mM) of 1-acetylene-1,4-butanediamine in 50 ml of ether containing 0.91 g (9.0 mM) of triethylamine is treated with 0.7 g (9.0 mM) of acetyl chloride. After 1 hour the ether solution is washed with brine, dried and evaporated to afford 1-acetylene-1,4-butylene-bis-acetamide.

When in the above procedure an appropriate amount of ethyl chloroformate is substituted for acetyl chloride, diethyl 1-acetylene-1,4-butylene-bis-carbamate is obtained.

We claim:

1. A compound of the formula

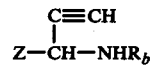

wherein Z is β-methylthioethyl, β-benzylthioethyl, S-(5′-desoxyadenosin-5′-yl)-S-methylthioethyl, γguanidinopropyl or

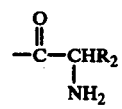

wherein n is the integer 2 or 3 and $R_1$ is hydrogen or a lower alkyl group of from 1 to 4 carbon atoms with the proviso that when $R_1$ is other than hydrogen, n is 2; each of $R_a$ and $R_b$ is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched or the group $$-\overset{O}{\underset{}{C}}-\underset{NH_2}{\overset{}{CHR_2}}$$

wherein $R_2$ is hydrogen, a straight or branched lower alkyl group of from 1 to 4 carbon atoms, benzyl or p-hydroxybenzyl; with the provisos that when Z is β-benzylthioethyl or S-(5′-desoxyadenosin-5′-yl)-S-methylthioethyl, $R_b$ is hydrogen, and when Z is

each of $R_a$ and $R_b$ can be the same or different; and pharmaceutically acceptable salts and individual optical isomers thereof.

2. A compound of claim 1 wherein Z is β-methylthioethyl, S-(5′-desoxyadenosin-5′-yl)-S-methylthioethyl, γ-guanidinopropyl or

3. A compound of claim 1 wherein each of $R_a$ and $R_b$ is hydrogen.

4. A compound of claim 1 wherein Z is

5. A compound of claim 4 wherein each of $R_a$ and $R_b$ is hydrogen.

6. A compound of claim 5 wherein $R_1$ is hydrogen or methyl.

7. A compound of claim 5 which is 1-acetylene-1,4-butanediamine.

8. A compound of claim 5 which is 1-acetylene-1,4-pentanediamine.

* * * * *